US009928590B2

(12) United States Patent
Kitamura et al.

(10) Patent No.: US 9,928,590 B2
(45) Date of Patent: Mar. 27, 2018

(54) IMAGE PROCESSING APPARATUS, IMAGE PROCESSING METHOD, AND COMPUTER-READABLE RECORDING DEVICE FOR DETERMINING WHETHER CANDIDATE REGION IS ABNORMALITY OR RESIDUE

(71) Applicant: OLYMPUS CORPORATION, Tokyo (JP)

(72) Inventors: Makoto Kitamura, Hachioji (JP); Yamato Kanda, Hino (JP); Takashi Kono, Tachikawa (JP); Masashi Hirota, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 2 days.

(21) Appl. No.: 14/519,538

(22) Filed: Oct. 21, 2014

(65) Prior Publication Data
US 2015/0063641 A1     Mar. 5, 2015

Related U.S. Application Data

(63) Continuation of application No. PCT/JP2013/061070, filed on Apr. 12, 2013.

(30) Foreign Application Priority Data

Apr. 23, 2012 (JP) ................................ 2012-098045

(51) Int. Cl.
*G06K 9/00* (2006.01)
*G06T 7/00* (2017.01)
*A61B 1/04* (2006.01)
*A61B 1/00* (2006.01)

(52) U.S. Cl.
CPC ........ *G06T 7/0014* (2013.01); *A61B 1/00009* (2013.01); *A61B 1/04* (2013.01);
(Continued)

(58) Field of Classification Search
None
See application file for complete search history.

(56) References Cited

U.S. PATENT DOCUMENTS 8,620,042 B2   12/2013   Kitamura et al.
8,811,698 B2   8/2014    Kono et al.
(Continued)

FOREIGN PATENT DOCUMENTS

JP   2005-192880 A   7/2005
JP   2011-521747 A   7/2011
(Continued)

OTHER PUBLICATIONS

Extended Supplementary European Search Report dated Jan. 5, 2016 from related European Application No. 13 78 2600.4.
(Continued)

*Primary Examiner* — Randolph I Chu
(74) *Attorney, Agent, or Firm* — Scully, Scott, Murphy & Presser, P.C.

(57) ABSTRACT

An image processing apparatus includes: an abnormality candidate region identifying unit configured to identify a candidate region for an abnormality from an image obtained by imaging inside of a lumen of a living body; a surrounding region determining unit configured to determine a surrounding region surrounding the candidate region; a shape information calculating unit configured to calculate shape information of the candidate region and shape information of the surrounding region in a depth direction with respect to a screen; and an abnormality region determining unit configured to determine whether or not the candidate region is an abnormality, based on a correlation between the shape information of the candidate region and the shape information of the surrounding region.

19 Claims, 17 Drawing Sheets

(52) U.S. Cl.
CPC ............... *G06T 2207/10068* (2013.01); *G06T 2207/20021* (2013.01); *G06T 2207/30028* (2013.01)

(56) References Cited

U.S. PATENT DOCUMENTS

| | | | |
|---|---|---|---|
| 2009/0074269 A1* | 3/2009 | Nishimura | A61B 1/04 382/128 |
| 2009/0306520 A1 | 12/2009 | Schmitt et al. | |
| 2011/0305388 A1 | 12/2011 | Wedi et al. | |

FOREIGN PATENT DOCUMENTS

| | | |
|---|---|---|
| JP | 2011-232715 A | 11/2011 |
| JP | 2012-045055 A | 3/2012 |
| WO | WO 2011/061940 A1 | 5/2011 |

OTHER PUBLICATIONS

Bernal, J., et al., "Integration of Valley Orientation Distribution for Polyp Region Identification in Colonoscopy", Sep. 18, 2011, Abdominal Imaging, Computational and Clinical Applications, pp. 76-83.

Nagakura, T., et al., "The study of three-dimensional measurement from an endoscopic images with stereo matching method", Jul. 1, 2006, World Automation Congress, pp. 1-4.

Yanai, H., et al., "Delineation of the gastric muscularis mucosae and assessment of depth of invasion of early gastric cancer using a 20-megahertz endoscopic ultrasound probe", Jan. 1, 1993, Gastrointestinal Endoscopy, vol. 39, No. 4.

International Search Report dated Jun. 18, 2013 issued in PCT/JP2013/061070.

\* cited by examiner

IMAGE PROCESSING APPARATUS, IMAGE PROCESSING METHOD, AND COMPUTER-READABLE RECORDING DEVICE FOR DETERMINING WHETHER CANDIDATE REGION IS ABNORMALITY OR RESIDUE

CROSS-REFERENCE TO RELATED APPLICATIONS

This application is a continuation of PCT international application Ser. No. PCT/JP2013/061070 filed on Apr. 12, 2013 which designates the United States, incorporated herein by reference, and which claims the benefit of priority from Japanese Patent Application No. 2012-098045, filed on Apr. 23, 2012, incorporated herein by reference.

BACKGROUND OF THE INVENTION

1. Field of the Invention

The disclosure relates to an image processing apparatus, an image processing method, and a computer-readable recording device, for identifying an abnormality region from an image obtained by imaging inside a lumen of a living body.

2. Description of the Related Art

As image processing for an image (hereinafter, referred to as "intraluminal image" or simply "image") obtained by imaging inside a lumen of a living body by a medical observation apparatus, such as an endoscope, a capsule endoscope, or the like, Japanese Patent Application Laid-open No. 2005-192880 discloses a technique for detecting an abnormality region based on color tone information of the image. In more detail, according to Japanese Patent Application Laid-open No. 2005-192880, a pixel value of each pixel in the image is mapped into a feature space based on color feature data and clustered in the feature space, and thereafter, based on information on a size, gravity center coordinates, and the like of each cluster, a normal mucosa cluster and an abnormality cluster are identified and a pixel region belonging to the abnormality cluster is detected as an abnormality region.

SUMMARY OF THE INVENTION

In accordance with some embodiments, an image processing apparatus, an image processing method, and a computer-readable recording device are presented.

In some embodiments, an image processing apparatus includes: an abnormality candidate region identifying unit configured to identify a candidate region for an abnormality from an image obtained by imaging inside of a lumen of a living body; a surrounding region determining unit configured to determine a surrounding region surrounding the candidate region; a shape information calculating unit configured to calculate shape information of the candidate region and shape information of the surrounding region in a depth direction with respect to a screen; and an abnormality region determining unit configured to determine whether or not the candidate region is an abnormality, based on a correlation between the shape information of the candidate region and the shape information of the surrounding region.

In some embodiments, an image processing method includes: identifying a candidate region for an abnormality from an image obtained by imaging inside of a lumen of a living body; determining a surrounding region surrounding the candidate region; calculating shape information of the candidate region and shape information of the surrounding region in a depth direction with respect to a screen; and determining whether or not the candidate region is an abnormality, based on a correlation between the shape information of the candidate region and the shape information of the surrounding region.

In some embodiments, a computer-readable recording device is a recording device with an executable program stored thereon. The program instructs a processor to perform: identifying a candidate region for an abnormality from an image obtained by imaging inside of a lumen of a living body; determining a surrounding region surrounding the candidate region; calculating shape information of the candidate region and shape information of the surrounding region in a depth direction with respect to a screen; and determining whether or not the candidate region is an abnormality, based on a correlation between the shape information of the candidate region and the shape information of the surrounding region.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Hereinafter, an image processing apparatus, an image processing method, and a computer-readable recording device according to some embodiments of the present invention will be described with reference to the drawings. The present invention is not to be limited by these embodiments. The same reference signs are used to refer to the same elements throughout the drawings.

In the embodiments below, as an example, a process for an intraluminal image (hereinafter, also simply referred to as "image") acquired by imaging inside a lumen of a living body by a medical observation apparatus, such as an endoscope or a capsule endoscope, will be described. In the description below, an image to be subjected to image processing is, for example, a color image, which has pixel levels (pixel values) of 256 gradations, for example, for each color component (wavelength component) of red (R), green (G), and blue (B) at each pixel position. Not being limited to an intraluminal image, the present invention may be widely applied to a case in which a particular region is to be extracted from an image acquired by another general image acquiring apparatus.

First Embodiment

Figure 1:
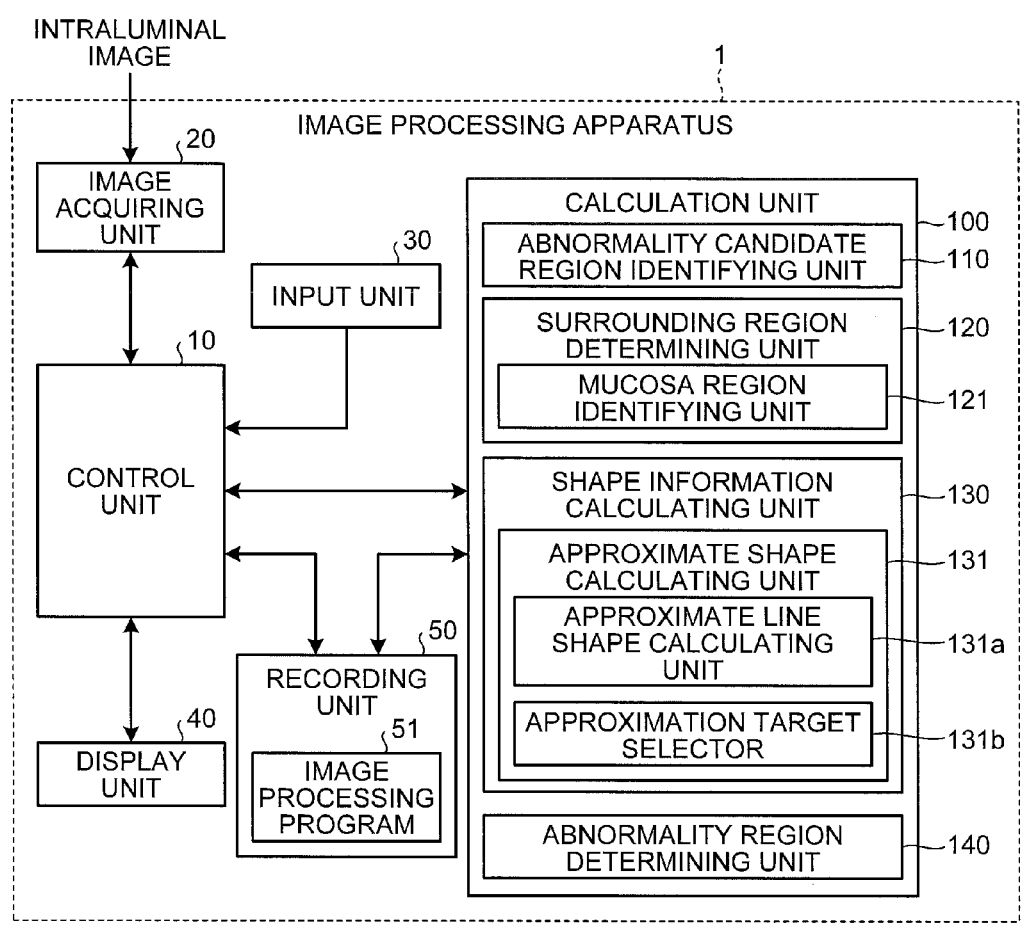
FIG. 1 is a block diagram illustrating a configuration of an image processing apparatus according to a first embodiment of the present invention.

FIG. 1 is a block diagram illustrating a configuration of an image processing apparatus according to a first embodiment of the present invention. An image processing apparatus 1 illustrated in FIG. 1 includes: a control unit 10 that controls operations of the whole image processing apparatus 1; an image acquiring unit 20 that acquires image data corresponding to an image captured by a medical observation apparatus; an input unit 30 that receives an input signal input from outside; a display unit 40 that performs various displays; a recording unit 50 that stores therein the image data acquired by the image acquiring unit 20 and various programs; and a calculation unit 100 that executes specified image processing on the image data.

The control unit 10 is realized by hardware, such as a CPU, and by reading the various programs recorded in the recording unit 50, performs transfer or the like of instructions and data to each unit forming the image processing apparatus 1 and comprehensively controls the operations of the whole image processing apparatus 1, according to the image data input from the image acquiring unit 20, an operation signal input from the input unit 30, or the like.

The image acquiring unit 20 is configured as appropriate according to a mode of a system including the medical observation apparatus. For example, if the medical observation apparatus is a capsule endoscope and a portable recording medium is used in transfer of image data to and from the medical observation apparatus, the image acquiring unit 20 is configured by a reader device, to which this recording medium is detachably attached, and which reads stored image data of an intraluminal image. Further, if a server that stores therein the image data of the intraluminal image captured by the medical observation apparatus is to be arranged, the image acquiring unit 20 is configured by a communication device or the like that is connected to the server and performs data communication with the server to acquire the image data of the intraluminal image. Or, the image acquiring unit 20 may be configured by an interface device or the like that inputs an image signal from the medical observation apparatus such as the endoscope via a cable.

The input unit 30 is realized by an input device, such as, for example, a keyboard and a mouse, a touch panel, or various switches, and outputs the received input signal to the control unit 10.

The display unit 40 is realized by a display device, such as an LCD or an EL display, and displays, under control by the control unit 10, various screens including an intraluminal image.

The recording unit 50 is realized by: various IC memories, such as a ROM and a RAM, which are rewritable flash memories or the like; a hard disk that is built therein or connected via a data communication terminal; an information recording device, such as a CD-ROM, and its reading device; or the like. The recording unit 50 stores therein the image data of the intraluminal image acquired by the image acquiring unit 20, as well as a program for causing the image processing apparatus 1 to operate and causing the image processing apparatus 1 to perform various functions, data used during execution of this program, and the like. Specifically, the recording unit 50 stores therein an image processing program 51 for detecting an abnormality of a white color tone, such as an aphthous lesion or ulcer from an image, various types of information to be used during execution of this program, and the like.

The calculation unit 100 is realized by hardware, such as a CPU, and by reading the image processing program 51, performs image processing on the image data corresponding to the intraluminal image, and executes various computing processes for detecting an abnormality of a white color tone, such as an aphthous lesion or ulcer.

Next, a detailed configuration of the calculation unit 100 will be described.

As illustrated in FIG. 1, the calculation unit 100 includes: an abnormality candidate region identifying unit 110 that identifies, from an intraluminal image, a candidate region for an abnormality; a surrounding region determining unit 120 that determines a surrounding region surrounding the candidate region; a shape information calculating unit 130 that calculates shape information of the candidate region and surrounding region in a depth direction with respect to a screen; and an abnormality region determining unit 140 that determines whether or not the candidate region is an abnormality, based on a correlation between the shape information of the candidate region and the shape information of the surrounding region.

The surrounding region determining unit 120 has a mucosa region identifying unit 121 that identifies a mucosa region included in an image, and determines a range of the surrounding region such that the surrounding region includes only the mucosa region.

The shape information calculating unit 130 has an approximate shape calculating unit 131 that approximates, based on pixel values of a plurality of pixels respectively included in the candidate region and surrounding region, shapes of the candidate region and surrounding region in the depth direction of the screen to specified shapes, respectively. In this first embodiment, the approximate shape calculating unit 131 includes: an approximate line shape calculating unit 131a that approximates shapes of the candidate region and surrounding region to one or more lines or curves; and an approximation target selector 131b that selects a target for which an approximate shape is to be calculated, based on information related to the pixels included in the candidate region and surrounding region.

Figure 2:
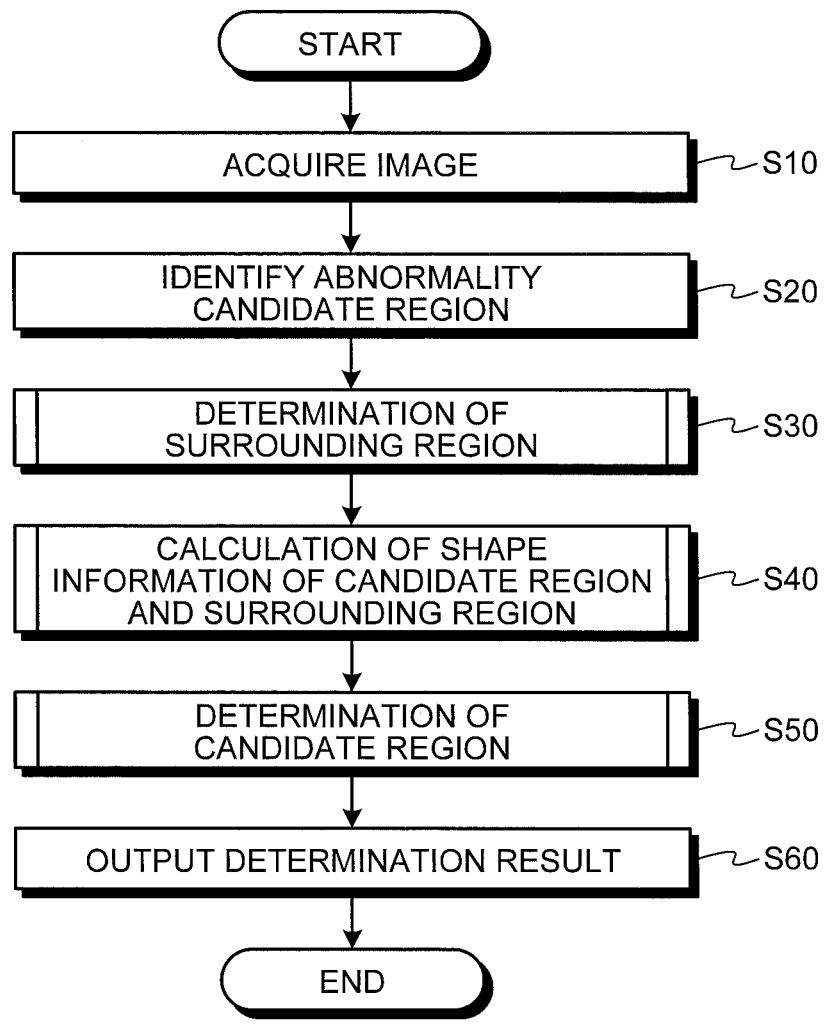
FIG. 2 is a flow chart illustrating operations of the image processing apparatus illustrated in FIG. 1.

Next, operations of the image processing apparatus 1 will be described. FIG. 2 is a flow chart illustrating the operations of the image processing apparatus 1.

Figure 3:
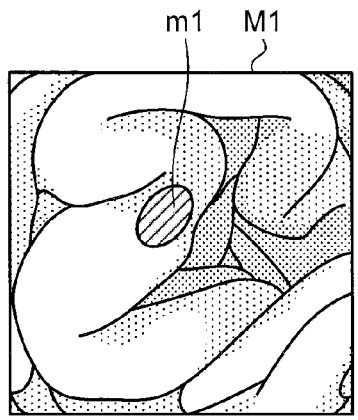
FIG. 3 is a schematic diagram illustrating an example of an image to be processed.

First, at Step S10, the image acquiring unit 20 acquires and records in the recording unit 50 an intraluminal image. The calculation unit 100 reads image data corresponding to an image to be processed from the recording unit 50. FIG. 3 is a schematic diagram illustrating an example of an image to be processed, that has been read by the calculation unit 100.

At subsequent Step S20, the abnormality candidate region identifying unit 110 identifies, based on color feature data of pixels in an image M1, a candidate region for an abnormality present in the image M1. Abnormalities, such as an aphthous lesion, an ulcer, and the like, indicate a particular color of a white color tone. Thus, the abnormality candidate region identifying unit 110 determines, based on a color range of a criterion for an abnormality region of a white tone determined beforehand, whether or not each pixel in the image M1 indicates a particular color likely to be an abnormality. This criterion for an abnormality region is determined based on respective pixel values of R, G, and B components of abnormality regions collected beforehand and color feature data secondarily calculated by a known conversion from these pixel values, and is recorded in the recording unit 50 beforehand. The color feature data may be values, such as color differences calculated by YCbCr conversion, hues, chromas calculated by HSI conversion, color ratios (G/R, B/G, or the like), or the like.

A pixel region identified as an abnormality by this identifying process is extracted as a candidate region for an abnormality. A region m1 illustrated in FIG. 3 represents an example of a candidate region.

A method of identifying a candidate region is not limited to the above method, and any method may be used, as long as a region of a particular color is able to be detected from an image. For example, various known detecting methods are usable, such as a method of threshold processing a distance in a color feature space between representative color feature data of an abnormality and color feature data of each pixel (k-nearest neighbor method, reference: Japanese Patent No. 4266920, "Digital Image Processing" by CG-ARTS Society, page 228 (NN method and kNN method)). Further, instead of using the color feature data of each pixel, after dividing the image into a plurality of small regions based on edge information or the like, color feature data in small region units may be used to detect a candidate region.

At subsequent Step S30, the surrounding region determining unit 120 determines a mucosal surface that is the same as the candidate region as a surrounding region surrounding the candidate region. In this first embodiment, a mucosa region at a short distance from the candidate region is determined as the surrounding region.

Figure 4:
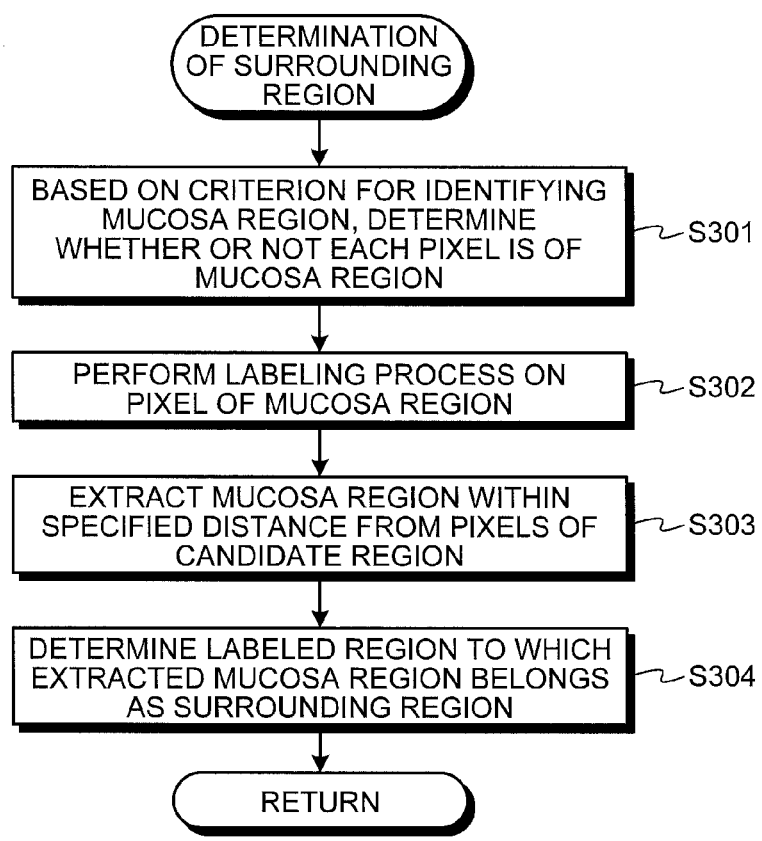
FIG. 4 is a flow chart illustrating a process of determining a surrounding region.

FIG. 4 is a flow chart illustrating a process of determining a surrounding region.

First, at Step S301, the mucosa region identifying unit 121 determines, based on a color range of a criterion for identifying a mucosa region determined beforehand, whether or not each pixel in the image M1 is of a mucosa region. This criterion for a mucosa region is determined based on respective pixel values of R, G, and B components of each pixel in a mucosa region and in a region other than a mucosa (non-mucosa region) collected beforehand and color feature data secondarily calculated by a known conversion from these pixel values, and is recorded in the recording unit 50 beforehand. The color feature data may be values, such as color differences calculated by YCbCr conversion, hues, chromas calculated by HSI conversion, color ratios (G/R, B/G, or the like), or the like.

At Step S302, the surrounding region determining unit 120 performs a labeling process on pixels identified as a mucosa region (reference: "Digital Image Processing" by CG-ARTS Society, pages 181 to 182 (Basic Processing, and Measurement and Labeling, of Binary Image)).

At Step S303, the surrounding region determining unit 120 extracts a mucosa region within a specified distance from each pixel of the candidate region in the image M1.

At subsequent Step S304, the surrounding region determining unit 120 determines a labeled region to which the extracted mucosa region belongs as a surrounding region. Thereafter, the process returns to a main routine.

At Step S40 subsequent to Step S30, the shape information calculating unit 130 calculates shape information in a depth direction of a screen, for each of the candidate region and surrounding region. In this first embodiment, shapes of the candidate region and surrounding region are approximated to lines, and information related to shapes of the approximated lines is acquired.

Figure 5:
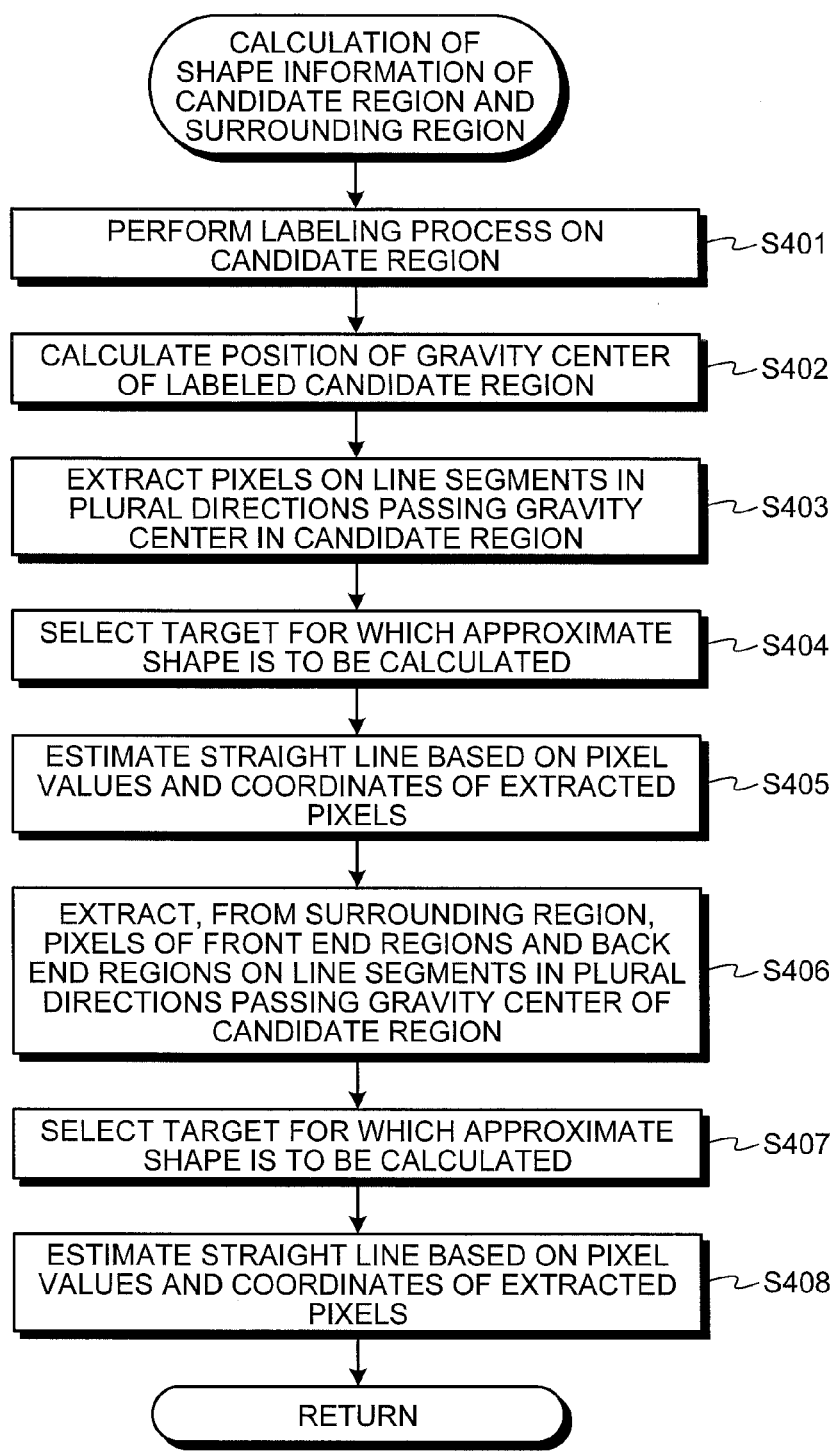
FIG. 5 is a flow chart illustrating a process of calculating shape information of a candidate region and a surrounding region.

FIG. 5 is a flow chart illustrating a process of calculating the shape information of the candidate region and surrounding region.

Figure 6:
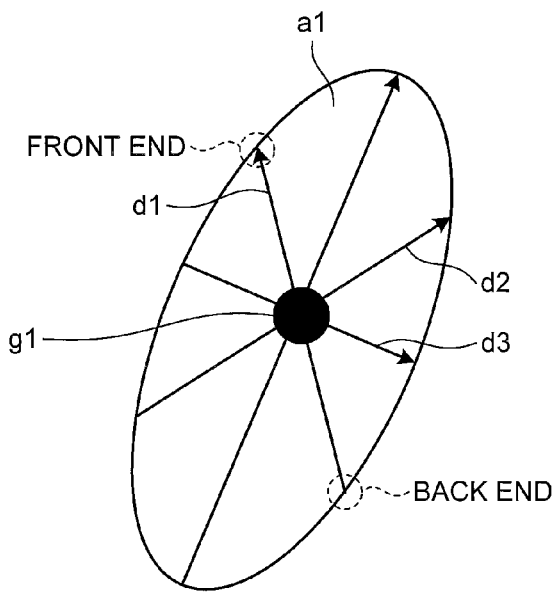
FIG. 6 is a schematic diagram illustrating a process of calculating shape information of a candidate region.

First, at Step S401, the approximate shape calculating unit 131 performs a labeling process on the candidate region identified in Step S20. FIG. 6 is a schematic diagram illustrating one of the labeled candidate regions. Hereinafter, as an example, a process for a candidate region a1 illustrated in FIG. 6 will be described.

At subsequent Step S402, the approximate shape calculating unit 131 calculates a coordinate gravity center (hereinafter, simply referred to as "gravity center") g1.

At Step S403, the approximate line shape calculating unit 131a extracts pixels on line segments in a plurality of directions d1, d2, . . . passing the gravity center g1 in the candidate region a1. For example, in FIG. 6, pixels of regions of line segments in respective directions d1 to d3 are extracted, the regions being between back ends and front ends at which the line segments intersect a contour of the candidate region. In FIG. 6, although the three directions d1 to d3 are exemplified, the set directions and the number of line segments are not particularly limited.

At Step S404, the approximation target selector 131b selects, based on the number of pixels extracted for each of the directions d1, d2, . . . , a target for which an approximate shape is to be calculated. Specifically, the approximation target selector 131b calculates an approximate shape for only the direction/directions having the number/numbers of extracted pixels equal to or greater than a specified value.

The direction having the number of pixel values less than the specified value may have a problem caused in reliability of approximation.

At Step S405, the approximate line shape calculating unit 131a estimates for each of the directions d1, d2, ..., based on pixel values and coordinates of the extracted pixels, a straight line indicating a change in distance in the depth direction of the screen, by a known method, such as a least squares method. As a quantity representing the distance in the depth direction, for example, an R-value of the pixel values is used. This is because R-value has the longest wavelength in the respective R, G, B, components and is difficult to be absorbed and scattered in a living body, and thus imaging from a close view to a distant view of an intraluminal image is possible in a state in which absorption and scattering of illumination light and reflected light are suppressed. As the quantity representing the change in the distance in the depth direction other than the R-value, G-value, B-value, luminance calculated from pixel values (respective values of R, G, and B components), or the like may be used.

Hereinafter, slopes of straight lines estimated for the directions d1, d2, ... are denoted by $\alpha 1$, $\alpha 2$, ..... The slopes $\alpha 1$, $\alpha 2$, ... of these straight lines are used as shape information of the candidate region a1.

Figure 7:
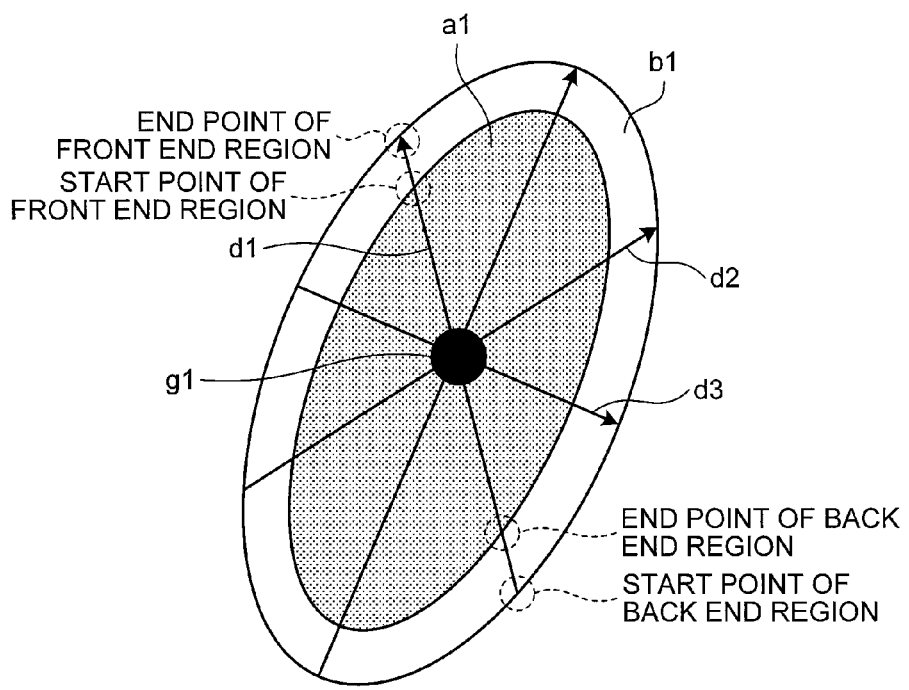
FIG. 7 is a schematic diagram illustrating a process of calculating shape information of a surrounding region.

At Step S406, the approximate line shape calculating unit 131a extracts, from each surrounding region, pixels of a front end region and a back end region of line segments in the plurality of directions d1, d2, ... passing the gravity center g1 of the candidate region. For example, as illustrated in FIG. 7, for a surrounding region b1 of the candidate region a1, with respect to each of the directions d1, d2, ..., pixel values and coordinates of pixels between a start point and an end point of a front end region and between a start point and an end point of a back end region are extracted. The start point of the front end region and the end point of the back end region are positions in contact with the candidate region a1. For the direction not determined to be the target for which an approximate shape is to be calculated in Step S404, extraction of pixels is not performed.

At Step S407, the approximation target selector 131b selects, based on the number of pixels extracted for each of the directions d1, d2, ... from the surrounding region b1, a target for which an approximate shape of the surrounding region is to be calculated. Specifically, the approximation target selector 131b calculates an approximate shape for only a direction having the number of extracted pixels equal to or greater than a specified value. This is because a direction having the number of pixel values less than the specified value may have a problem caused in reliability of approximation.

At Step S408, the approximate line shape calculating unit 131a estimates for each of the directions d1, d2, ..., based on pixels values and coordinates of the pixels extracted from the surrounding region, a straight line indicating a change in distance in the depth direction of the screen, by a known method, such as a least squares method. A quantity representing the change in distance used therefor is as described for Step S405. Hereinafter, slopes of the straight lines estimated for the directions d1, d2, ... are denoted by $\beta 1$, $\beta 2$, ..... The slopes $\beta 1$, $\beta 2$, ... of these straight lines are used as shape information of the surrounding region b1. Thereafter, the process returns to the main routine.

At Step S50 subsequent to Step S40, the abnormality region determining unit 140 determines, based on a correlation between the shape information of the candidate region and the shape information of the surrounding region, whether or not the candidate region is an abnormality.

Figure 8A:
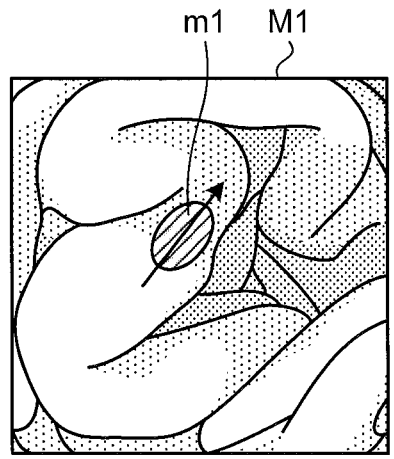
FIGS. 8A and 8B are schematic diagrams illustrating a process of determining a candidate region.
Figure 8B:
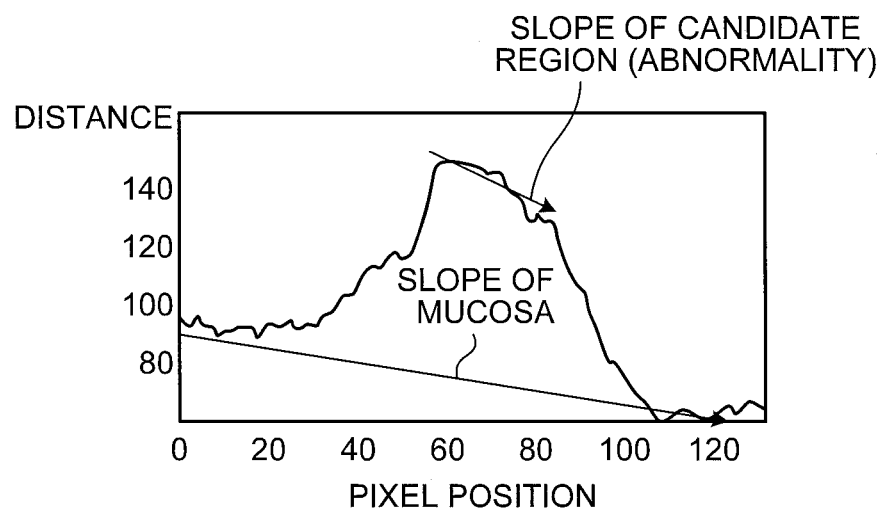
Figure 9A:
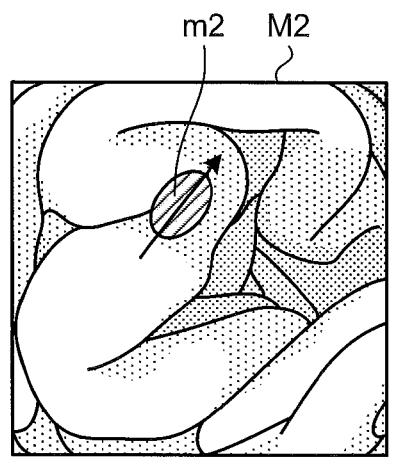
FIGS. 9A and 9B are schematic diagrams illustrating a process of determining a candidate region.
Figure 9B:
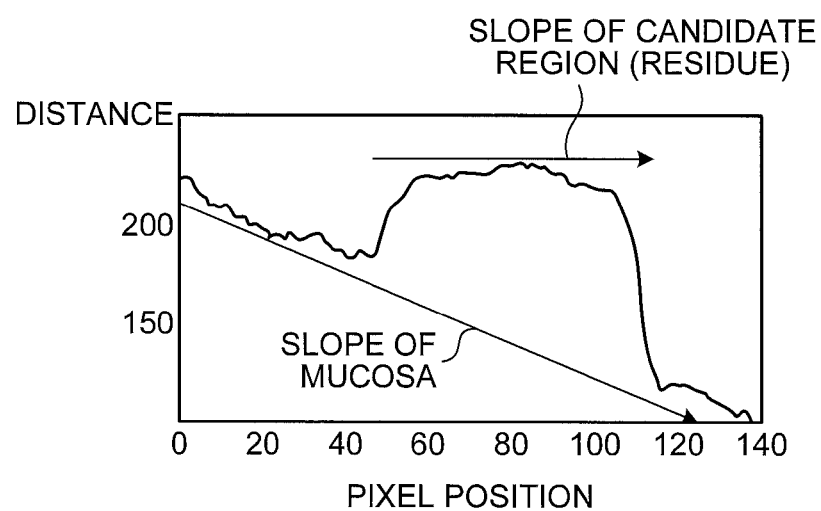

As illustrated in FIG. 8A, if the candidate region m1 detected from the image M1 is an abnormality present on a mucosal surface, like an aphthous lesion or ulcer, the shape information (slope of the straight line) of the candidate region m1 is in a state similar to that of the shape information of a surrounding mucosal surface (surrounding region), as illustrated in FIG. 8B. On the contrary, as illustrated in FIG. 9A, if a candidate region m2 detected from an image M2 is a residue floating in a lumen, shape information of the candidate region m2 becomes unrelated to shape information of a surrounding mucosal surface, as illustrated in FIG. 9B. Accordingly, the abnormality region determining unit 140 determines that the candidate region is an abnormality if the shape information of the candidate region and the shape information of the surrounding region are similar to each other, and determines that the candidate region is a floating residue if they are not similar to each other.

Figure 10:
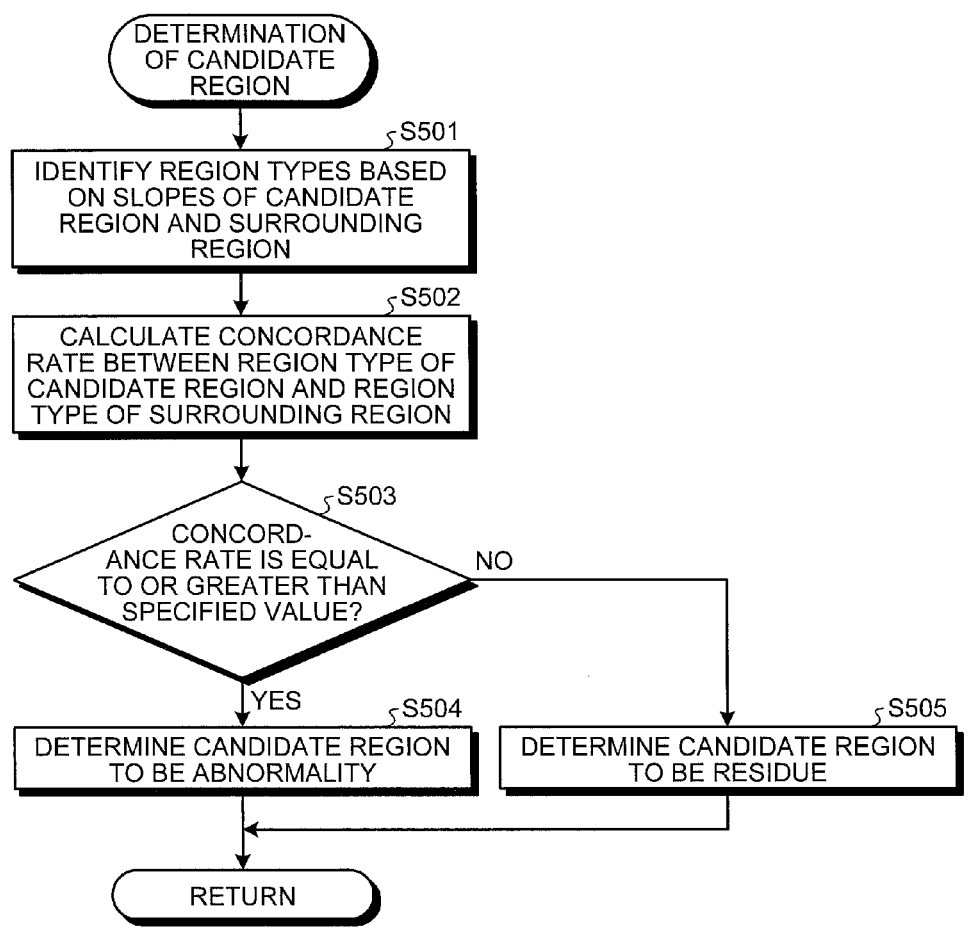
FIG. 10 is a flow chart illustrating a process of determining a candidate region.

FIG. 10 is a flow chart illustrating details of a process of determining a candidate region. Hereinafter, a process for the candidate region a1 illustrated in FIG. 6 and the surrounding region b1 illustrated in FIG. 7 will be described.

At Step S501, the abnormality region determining unit 140 identifies, for each direction, region types of the candidate region a1 and surrounding region b1 as follows, based on the slopes $\alpha 1$, $\alpha 2$, ... in the respective directions d1, d2, ... of the candidate region and the slopes $\beta 1$, $\beta 2$, ... in the respective directions d1, d2, ... of the surrounding region.

If slope is equal to or greater than specified threshold value T1 and less than specified threshold value T2: flat region If slope is equal to or greater than specified threshold value T2: sloped region in plus direction If slope is less than specified threshold value T1: sloped region in minus direction Herein, the respective threshold values are set at values satisfying T1<T2.

At subsequent Step S502, the abnormality region determining unit 140 calculates a concordance rate between the region type of the candidate region a1 and the region type of the surrounding region b1 in the same direction. For example, in the certain direction d1, if the candidate region a1 is identified as a sloped region in the plus direction while the surrounding region b1 is identified as a sloped region in the minus direction, these two are determined as not matching each other. Or, if in the certain direction d1, the candidate region a1 and the surrounding region b1 are both identified as flat regions (or both are sloped regions in the plus or minus direction), these two are determined as matching each other. The abnormality region determining unit 140 determines for each direction whether or not the region type of the candidate region a1 and the region type of the surrounding region b1 match each other. In all of the directions d1, d2, ..., for which the shape information has been calculated, a proportion (concordance rate) of the number of directions in which the region type of the candidate region a1 and the region type of the surrounding region b1 match each other is calculated.

At Step S503, the abnormality region determining unit 140 determines whether or not the concordance rate calculated in Step S502 is equal to or greater than a specified value. If the concordance rate is equal to or greater than the specified value (Step S503: Yes), the abnormality region determining unit 140 determines that the candidate region is an abnormality (Step S504). On the contrary, if the concordance rate is less than the specified value (Step S503: No), the abnormality region determining unit 140 determines that the candidate region is a residue (Step S505). Thereafter, the process returns to the main routine.

At Step S60 subsequent to Step S50, the calculation unit 100 outputs a result of the determination in Step S50. Accordingly, the control unit 10 records the determination result for an abnormality in the recording unit 50. The control unit 10 may cause the display unit 40 or the like to display the determination result for an abnormality. Thereafter, the process in the image processing apparatus 1 is ended.

As described above, according to the first embodiment, after detecting a candidate region for an abnormality based on color feature data of pixels, from an image to be processed, by calculating shape information of the candidate region and its surrounding region in a depth direction, and comparing the shape information of the candidate region with the shape information of the surrounding region, an abnormality and another object having the same type of color information as that of the abnormality are able to be accurately distinguished from each other.

First Modified Example

Next, a first modified example of the first embodiment will be described.

Figure 11:
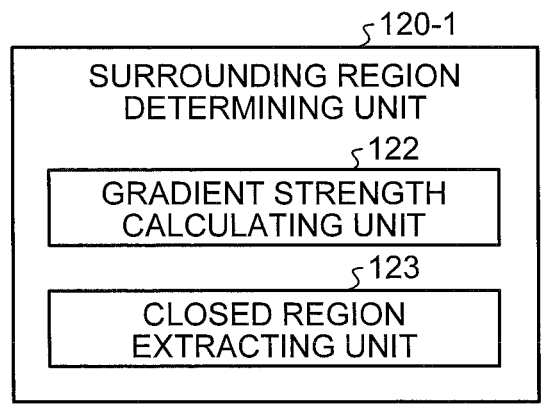
FIG. 11 is a block diagram illustrating a configuration of a surrounding region determining unit according to a first modified example of the first embodiment.

FIG. 11 is a block diagram illustrating a configuration of a surrounding region determining unit included in an image processing apparatus according to the first modified example. The image processing apparatus according to the first modified example includes a surrounding region determining unit 120-1 illustrated in FIG. 11, instead of the surrounding region determining unit 120 illustrated in FIG. 1. A configuration of the image processing apparatus other than the surrounding region determining unit 120-1 is similar to that illustrated in FIG. 1.

The surrounding region determining unit 120-1 has a gradient strength calculating unit 122 and a closed region extracting unit 123, and determines a closed region, which includes a candidate region detected from an image and does not include a region in which a gradient strength of a groove or the like is high, as a surrounding region.

Figure 12:
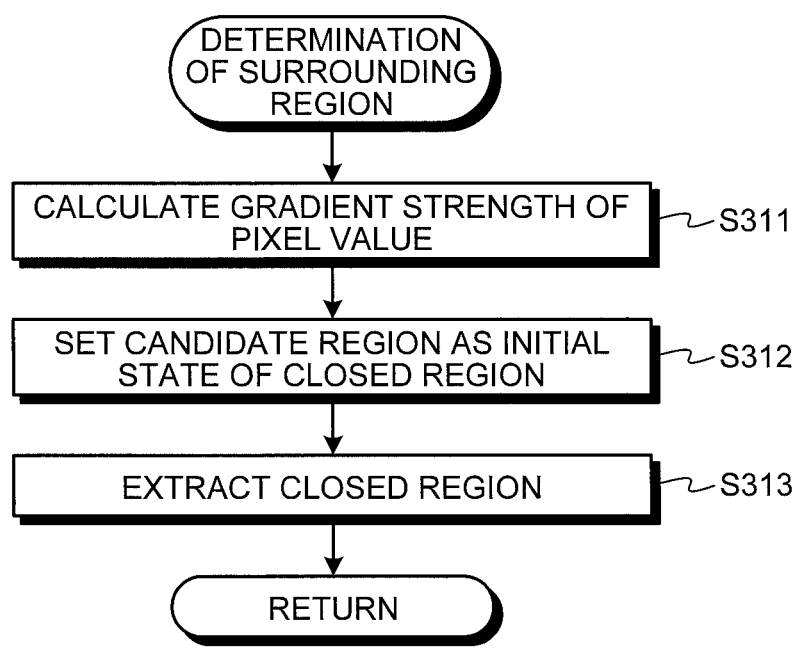
FIG. 12 is a flow chart illustrating operations of the surrounding region determining unit illustrated in FIG. 11.

FIG. 12 is a flow chart illustrating operations of the surrounding region determining unit 120-1. Operations of the whole image processing apparatus according to the first modified example are similar to those illustrated in FIG. 2.

First, at Step S311, the gradient strength calculating unit 122 calculates a gradient strength, based on pixel values (respective values of R, G, and B components) of respective pixels in an image to be processed, or values of luminance or the like calculated from these pixel values. The gradient strength is able to be calculated by a known method, such as Laplacian filtering, Sobel filtering, or the like (reference: "Digital Image Processing" by CG-ARTS Society, pages 114 to 121 (Edge Extraction)).

At subsequent Step S312, the closed region extracting unit 123 sets a candidate region as an initial state of a closed region.

Further, at Step S313, the closed region extracting unit 123 sets an energy function such that a region of pixels having a gradient strength equal to or greater than a specified value is not included inside, expands the closed region from the initial state based on a value of the energy function, and extracts the closed region (reference: "Digital Image Processing" by CG-ARTS Society, pages 197 to 198).

As the energy function, for example, a weighted sum of four energies, which are an edge inclusion energy corresponding to an energy defined by a gradient strength of pixels of a closed region, an internal energy and an external energy corresponding to an energy defined by an external form of the closed region, and an image energy corresponding to an energy defined by the gradient strength of the pixels of the closed region. Of these, the edge inclusion energy is an energy that indicates a larger value as the gradient strength in the closed region gets larger. The internal energy is an energy that represents smoothness of a boundary of the closed region and indicates a smaller value as shape of the closed region gets smoother. The external energy is an energy that indicates a smaller value as size of the closed region gets larger. The image energy is an energy that indicates a smaller value as value of the gradient strength at the boundary of the closed region gets larger.

The closed region extracting unit 123 arranges a plurality of control points on the boundary of the closed region in the initial state, calculates, for each of the control points, the edge inclusion energy, internal energy, image energy, and external energy from a position of each of the control points, a gradient strength at that position, a distance of each of the control points from a gravity center, a gradient strength of pixels inside, or the like, and performs deformation in a direction where the closed region is extended, by moving the control points such that the weighted sum of these four energies is minimized. The surrounding region determining unit 120-1 determines the closed region extracted as above, as a surrounding region.

Second Modified Example

Next, a second modified example of the first embodiment will be described.

Figure 13:
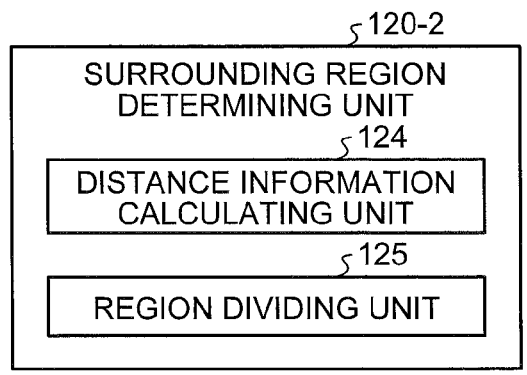
FIG. 13 is a block diagram illustrating a configuration of a surrounding region determining unit according to a second modified example of the first embodiment.

FIG. 13 is a block diagram illustrating a configuration of a surrounding region determining unit included in an image processing apparatus according to the second modified example. The image processing apparatus according to the second modified example includes a surrounding region determining unit 120-2 illustrated in FIG. 13, instead of the surrounding region determining unit 120 illustrated in FIG. 1. A configuration of the image processing apparatus other than the surrounding region determining unit 120-2 is similar to that illustrated in FIG. 1.

The surrounding region determining unit 120-2 has a distance information calculating unit 124 and a region dividing unit 125, and determines a region, which exists at a position near a candidate region detected from an image and has distance information (depth information) in the image, the distance information being similar to that of the candidate region, as a surrounding region.

Figure 14:
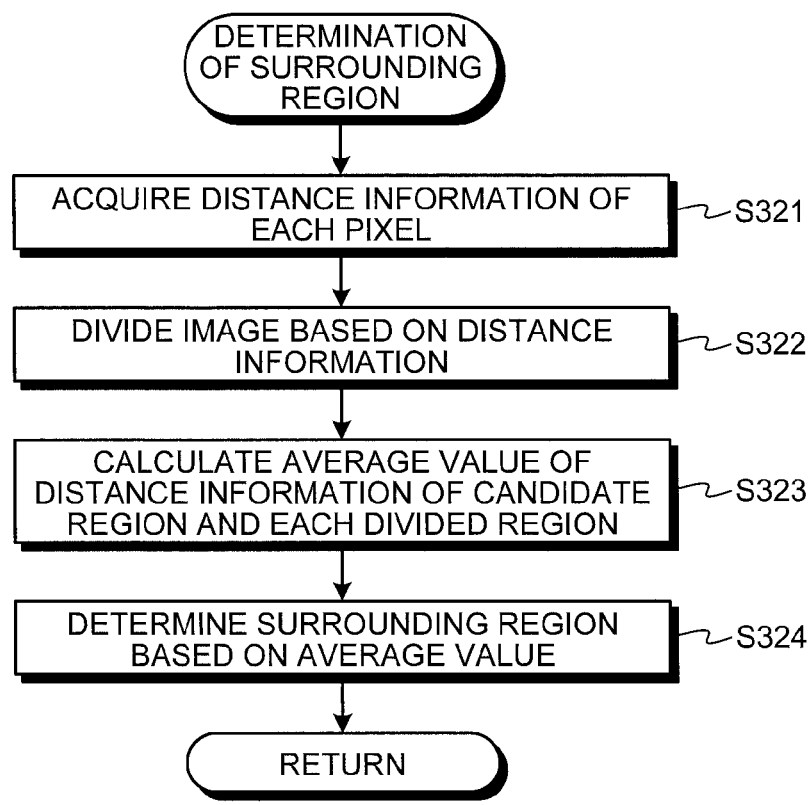
FIG. 14 is a flow chart illustrating operations of the surrounding region determining unit illustrated in FIG. 13.

FIG. 14 is a flow chart illustrating operations of the surrounding region determining unit 120-2. Operations of the whole image processing apparatus according to the second modified example are similar to those illustrated in FIG. 2.

First, at Step S321, the distance information calculating unit 124 acquires distance information of each pixel in an image. As the distance information, an R-value, which is a wavelength component that is hard to be absorbed and scattered in a body, luminance calculated from pixel values (respective values of R, G, and B components), or the like, is used.

At subsequent Step S322, the region dividing unit 125 divides, based on the distance information, the image into a plurality of regions. In this second modified example, region division is performed by combining pixels that have distance information similar to each other and are adjacent to each other by a region integration method using the distance information as feature data (reference: "Digital Image Processing" by CG-ARTS Society, page 196 (Region Division Process)). Any method other than the region integration method may be used, as long as the image is able to be divided into a plurality of regions based on the distance information.

At Step S323, the surrounding region determining unit 120-2 calculates an average value of distance information in the candidate region detected in Step S20 and in each divided region divided in Step S322.

At Step S324, the surrounding region determining unit 120-2 determines a divided region, which is present within a specified range from each pixel in the candidate region and in which a difference from the average value of the distance information of the candidate region is within a specified range, as a surrounding region.

Third Modified Example

Next, a third modified example of the first embodiment will be described.

Figure 15:
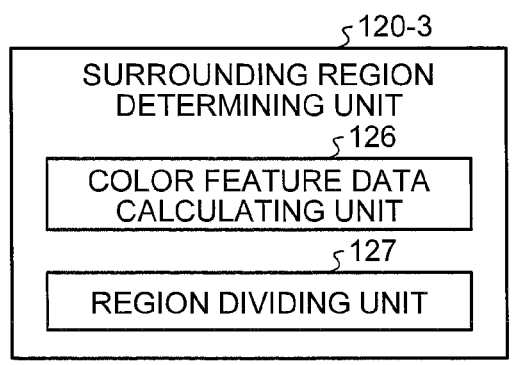
FIG. 15 is a block diagram illustrating a configuration of a surrounding region determining unit according to a third modified example of the first embodiment.

FIG. 15 is a block diagram illustrating a configuration of a surrounding region determining unit included in an image processing apparatus according to the third modified example. The image processing apparatus according to the third modified example includes a surrounding region determining unit 120-3 illustrated in FIG. 15, instead of the surrounding region determining unit 120 illustrated in FIG. 1. A configuration of the image processing apparatus other than the surrounding region determining unit 120-3 is similar to that illustrated in FIG. 1.

The surrounding region determining unit 120-3 has a color feature data calculating unit 126 and a region dividing unit 127, and determines a region, which is present at a position near a candidate region detected from an image and has color feature data similar to those of the candidate region, as a surrounding region.

Figure 16:
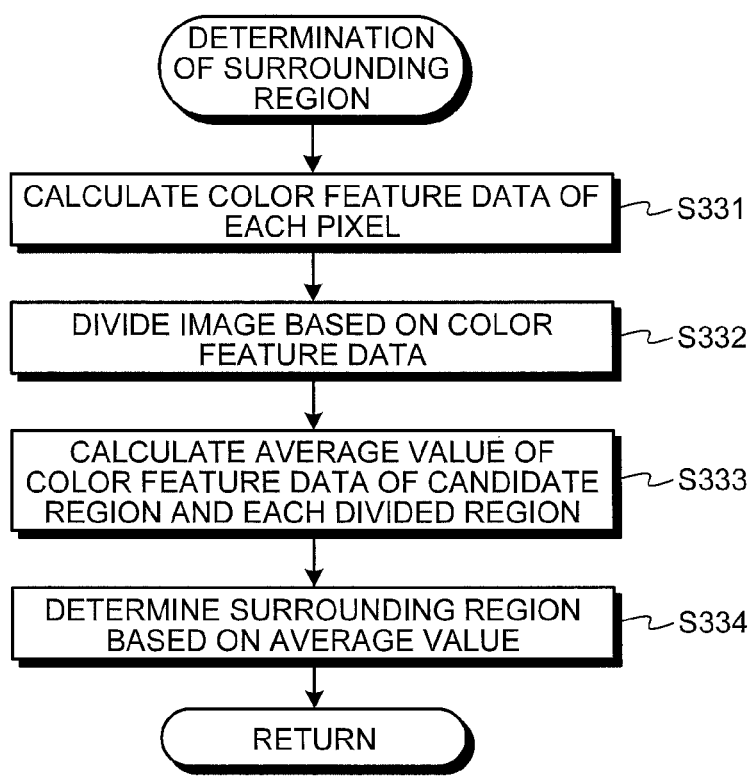
FIG. 16 is a flow chart illustrating operations of the surrounding region determining unit illustrated in FIG. 15.

FIG. 16 is a flow chart illustrating operations of the surrounding region determining unit 120-3. Operations of the whole image processing apparatus according to the third modified example are similar to those illustrated in FIG. 2.

First, at Step S331, the color feature data calculating unit 126 calculates color feature data of each pixel in an image. The color feature data may be color differences calculated from YCbCr conversion of pixel values, hue, chroma calculated by HSI conversion, color ratios (G/R or B/G), or the like, At subsequent Step S332, the region dividing unit 127 divides the image into a plurality of regions, based on the color feature data. In the third modified example, by a region integration method using the color feature data as feature data, pixels, which have color feature data similar to each other and are adjacent to each other, are integrated to thereby perform region division. Any method other than the region integration method may be used, as long as the image is able to be divided into a plurality of regions based on the color feature data.

At Step S333, the surrounding region determining unit 120-3 calculates an average value of the color feature data in the candidate region detected in Step S20 and in each divided region divided in Step S332.

At Step S334, the surrounding region determining unit 120-3 determines a divided region, which is present within a specified range from each pixel in the candidate region and in which a difference from the average value of the color feature data of the candidate region is within a specified range, as a surrounding region.

Fourth Modified Example

Next, a fourth modified example of the first embodiment will be described.

Figure 17:
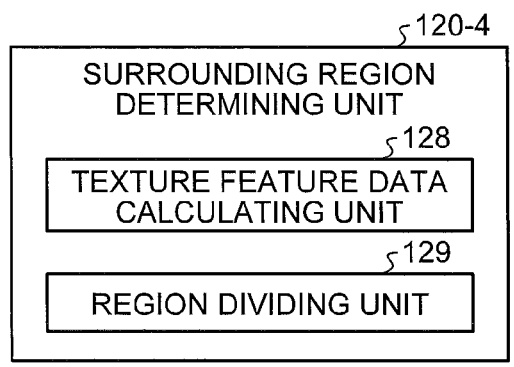
FIG. 17 is a block diagram illustrating a configuration of a surrounding region determining unit according to a fourth modified example of the first embodiment.

FIG. 17 is a block diagram illustrating a configuration of a surrounding region determining unit included in an image processing apparatus according to the fourth modified example. The image processing apparatus according to the fourth modified example includes a surrounding region determining unit 120-4 illustrated in FIG. 17, instead of the surrounding region determining unit 120 illustrated in FIG. 1. A configuration of the image processing apparatus other than the surrounding region determining unit 120-4 is similar to that illustrated in FIG. 1.

The surrounding region determining unit 120-4 has a texture feature data calculating unit 128 and a region dividing unit 129, and determines a region, which is present at a position near a candidate region detected from an image and has texture feature data similar to those of the candidate region, as a surrounding region.

Figure 18:
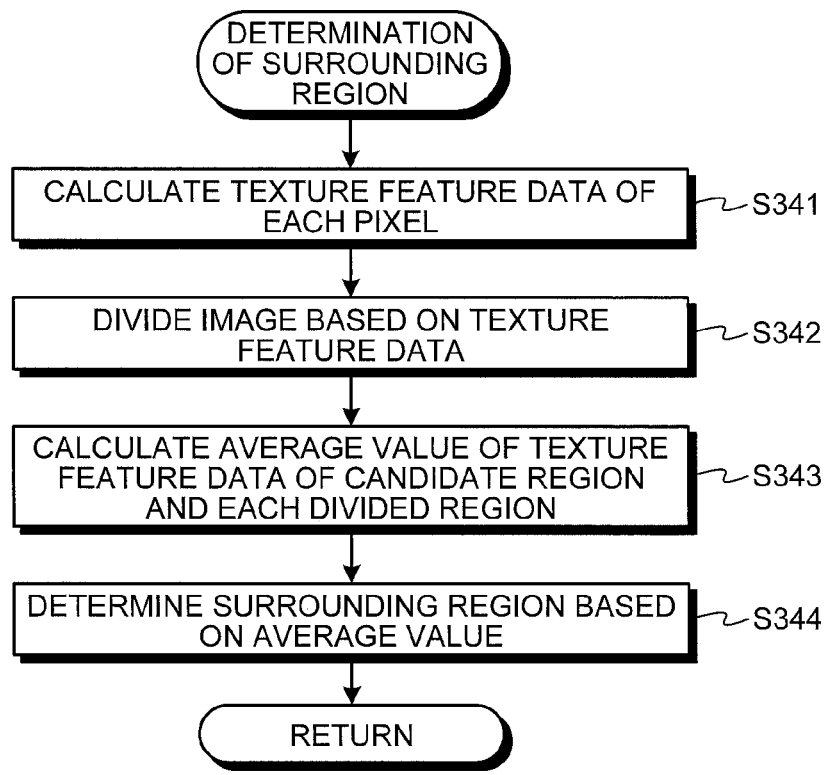
FIG. 18 is a flow chart illustrating operations of the surrounding region determining unit illustrated in FIG. 17.

FIG. 18 is a flow chart illustrating operations of the surrounding region determining unit 120-4. Operations of the whole image processing apparatus according to the fourth modified example are similar to those illustrated in FIG. 2.

First, at Step S341, the texture feature data calculating unit 128 calculates texture feature data in an image. As the texture feature data, for example, size of a particular frequency component calculated by discrete cosine transform (DCT), discrete Fourier transform (DFT), Gabor filtering, or the like, is used.

At subsequent Step S342, the region dividing unit 129 divides, based on the texture feature data, the image into a plurality of regions. In this fourth modified example, by a region integration method using the texture feature data as feature data, pixels, which have texture feature data similar to each other and are adjacent to each other, are integrated to thereby perform region division. Any method other than the region integration method may be used, as long as the image is able to be divided into a plurality of regions based on the texture feature data.

At Step S343, the surrounding region determining unit 120-4 calculates average values of the texture feature data in the candidate region detected in Step S20 and in each divided region divided in Step S342.

At Step S344, the surrounding region determining unit 120-4 determines the divided region, which is present within a specified range from each pixel in the candidate region and in which a difference from the average value of texture information of the candidate region is within a specified range, as a surrounding region.

Fifth Modified Example

Next, a fifth modified example of the first embodiment will be described.

In the first embodiment, the shape information calculating unit 130 approximates the shapes of the candidate region and surrounding region in the depth direction to one or more straight lines. However, the shapes of the candidate region and surrounding region in the depth direction may be approximated to one or more curves. For example, they may be approximated to a parabola shape represented by a quadratic function indicated by the following equation.

$$z = ax^2 + by + c$$

In the above equation, "x" indicates a coordinate of a pixel in each direction (see FIG. 6) passing a gravity center of a candidate region, and "z" indicates a value representing a distance of the pixel in the depth direction (for example, an R-value, luminance, or the like). Further, "a", "b", and "c" are coefficients (constants).

In this case, the abnormality region determining unit 140 uses the quadratic coefficient "a" as shape information, and based on whether or not a difference between the coefficients "a" of the candidate region and surrounding region is within a specified range, a concordance rate between the candidate region and surrounding region may be determined.

Sixth Modified Example

Next, a sixth modified example of the first embodiment will be described.

In the first embodiment, the abnormality region determining unit 140 calculates the concordance rate between the region types of the candidate region and surrounding region after identifying the region types of the candidate region and surrounding region in the respective directions. However, slopes of the candidate region and surrounding region may be directly compared for each direction and a concordance rate therebetween may be calculated.

Specifically, if the candidate region a1 illustrated in FIG. 6 and the surrounding region b1 illustrated in FIG. 7 are described as an example, first, differences $|\alpha 1 - \beta 1|$, $|\alpha 2 - \beta 2|$, ... between slopes of straight lines to which the candidate region is approximated and slopes of straight lines to which the surrounding region is approximated, are calculated, for respective directions, d1, d2, ... passing the gravity center g1 of the candidate region. Subsequently, each of the differences $|\alpha 1 - \beta 1|$, $|\alpha 2 - \beta 2|$, ... is compared with a specified threshold value, and if a difference becomes equal to or less than the threshold value, the slopes of the candidate region and surrounding region are determined as matching each other. A proportion (concordance rate) of the number of directions in which the slopes of the candidate region a1 and surrounding region b1 matched each other, of all of the directions d1, d2, ... for which shape information of the candidate region and surrounding region has been calculated, is calculated.

Second Embodiment

Next, a second embodiment of the present invention will be described.

Figure 19:
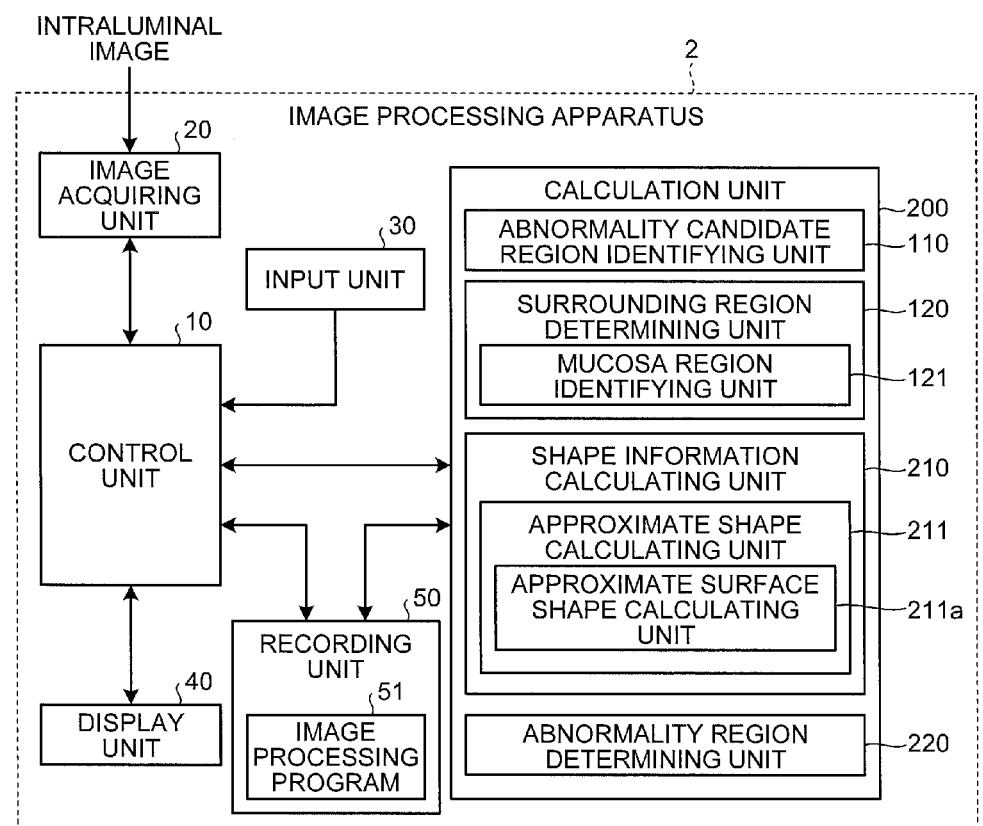
FIG. 19 is a block diagram illustrating a configuration of an image processing apparatus according to a second embodiment of the present invention.

FIG. 19 is a block diagram illustrating a configuration of an image processing apparatus according to the second embodiment of the present invention. As illustrated in FIG. 19, an image processing apparatus 2 according to the second embodiment includes a calculation unit 200, instead of the calculation unit 100 illustrated in FIG. 1.

The calculation unit 200 includes a shape information calculating unit 210 and an abnormality region determining unit 220, instead of the shape information calculating unit 130 and abnormality region determining unit 140 illustrated in FIG. 1. A configuration of each unit of the calculation unit 200 and image processing apparatus 2, other than the shape information calculating unit 210 and abnormality region determining unit 220, is similar to that of the first embodiment.

The shape information calculating unit 210 has a approximate shape calculating unit 211, which respectively approximates, based on pixel values of pixels in a candidate region detected from an image to be processed and in its surrounding region, shapes of the candidate region and surrounding region in a depth direction of a screen to specified shapes. In this second embodiment, the approximate shape calculating unit 211 includes an approximate surface shape calculating unit 211a that approximates, for each of the candidate region and surrounding region, a shape thereof in the depth direction, to a two-dimensional surface.

The abnormality region determining unit 220 performs, based on approximate shapes of the candidate region and surrounding region that have been approximated to two-dimensional surfaces by the shape information calculating unit 210, whether or not the candidate region is an abnormality.

Next, operations of the image processing apparatus 2 will be described. The operations of the image processing apparatus 2 are similar to those illustrated in FIG. 2 as a whole, and detailed operations thereof in a process of calculating shape information of a candidate region and a surrounding region (Step S40) and a process of determining a candidate region (Step S50) are different from those of the first embodiment.

At Step S40, the approximate surface shape calculating unit 211a calculates a function that approximates, based on pixel values of pixels included in each of the candidate region and surrounding region, each region. In this second embodiment, each region is approximated by a quadratic function given by Equation (1) below.

$$z = ax^2 + by^2 + cxy + dx + ey + f \qquad (1)$$

In Equation (1), (x, y) are coordinates of each pixel in an image. Further, "z" is a quantity representing distance in the depth direction of the screen, and preferably, an R-value of each pixel is used therefor. Otherwise, as a value of "z", a G-value or B-value of each pixel, luminance secondarily calculated from pixel values of each pixel (respective values of R, G, and B components), or the like may be used. Hereinafter, values including these values will be referred to as pixel values.

Further, "a" to "f" are coefficients (constants), and for example, are able to be calculated by solving Equation (2) below given by using coordinates $(x_i, y_i)$ of an i-th pixel (i=1, 2, ...) in an image and a pixel value $z_i$ of that pixel by a least squares method.

$$\begin{bmatrix} a \\ b \\ c \\ d \\ e \\ f \end{bmatrix} = (A^t \times A)^{-1} \times A^t \times \begin{bmatrix} z_1 \\ z_2 \\ \vdots \\ z_3 \end{bmatrix}, \text{ where} \qquad (2)$$

$$A = \begin{bmatrix} x_1^2 & y_1^2 & x_1 y_1 & x_1 & y_1 & 1 \\ x_2^2 & y_2^2 & x_2 y_2 & x_2 & y_2 & 1 \\ \vdots & \vdots & \vdots & \vdots & \vdots & \vdots \\ x_n^2 & y_n^2 & x_n y_n & x_n & y_n & 1 \end{bmatrix}$$

An approximation function acquired as above is used as shape information.

At subsequent Step S50, the abnormality region determining unit 220 determines, based on a correlation between the shape information of the candidate region and the shape information of the surrounding region, whether or not the candidate region is an abnormality. In more detail, the abnormality region determining unit 220 first calculates image regions of the same size, obtained by normalizing a two-dimensional region represented by the approximation function of the candidate region and a two-dimensional region represented by the approximation function of the surrounding region. Pixel values of pixels corresponding between these image regions are then estimated and a correlation between the pixel values is calculated.

Specifically, a square-sum SSD of differences between the pixel values given by Equation (3) below is calculated.

$$SSD = \sum_{y=0}^{Y-1} \sum_{x=0}^{X-1} (P_{I(k)}(x, y) - P_{I(j)}(x, y))^2 \quad (3)$$

In Equation (3), $P_{I(j)}(x, y)$ represents a pixel value at coordinates (x, y) of an image region I(j) obtained by normalizing an approximation function of a candidate region, and $P_{I(k)}$ represents a pixel value at coordinates (x, y) of an image region I(k) obtained by normalizing an approximation function of a surrounding region surrounding the candidate region. Further, "X" represents size of the image regions I(j) and I(k) in an x-direction, and "Y" indicates size of the image regions I(j) and I(k) in a y-direction.

If a value of the square-sum SSD is equal to or less than a specified value, the abnormality region determining unit 220 determines that the correlation between the shape information of the candidate region and the shape information of the surrounding region is high (that is, their similarity is high) and that the candidate region is an abnormality, such as an aphthous lesion or ulcer. On the contrary, if the square-sum SSD is greater than the specified value, the abnormality region determining unit 220 determines that the correlation between the shape information of the candidate region and the shape information of the surrounding region is low (that is, the similarity is low), and that the candidate region is a floating residue.

The abnormality region determining unit 220 may calculate, instead of calculating the square-sum SSD, a sum SAD of absolute values of differences between the pixel values represented by Equation (4) below, and may determine, based on this sum SAD, a correlation between the shape information of the candidate region and the shape information of the surrounding region.

$$SAD = \sum_{y=0}^{Y-1} \sum_{x=0}^{X-1} |P_{I(k)}(x, y) - P_{I(j)}(x, y)| \quad (4)$$

Further, the method of determining an abnormality is not limited to the method of using the square-sum SSD or the sum SAD of the absolute values of the differences, and any method may be used, as long as a correlation (similarity) between the shape information of the candidate region and the shape information of the surrounding region is able to be calculated. For example, normalized cross-correlation (reference: "Digital Image Processing" by CG-ARTS Society, pages 203 to 204 (Pattern Detection)) or the like may be used.

Third Embodiment

Next, a third embodiment of the present invention will be described.

Figure 20:
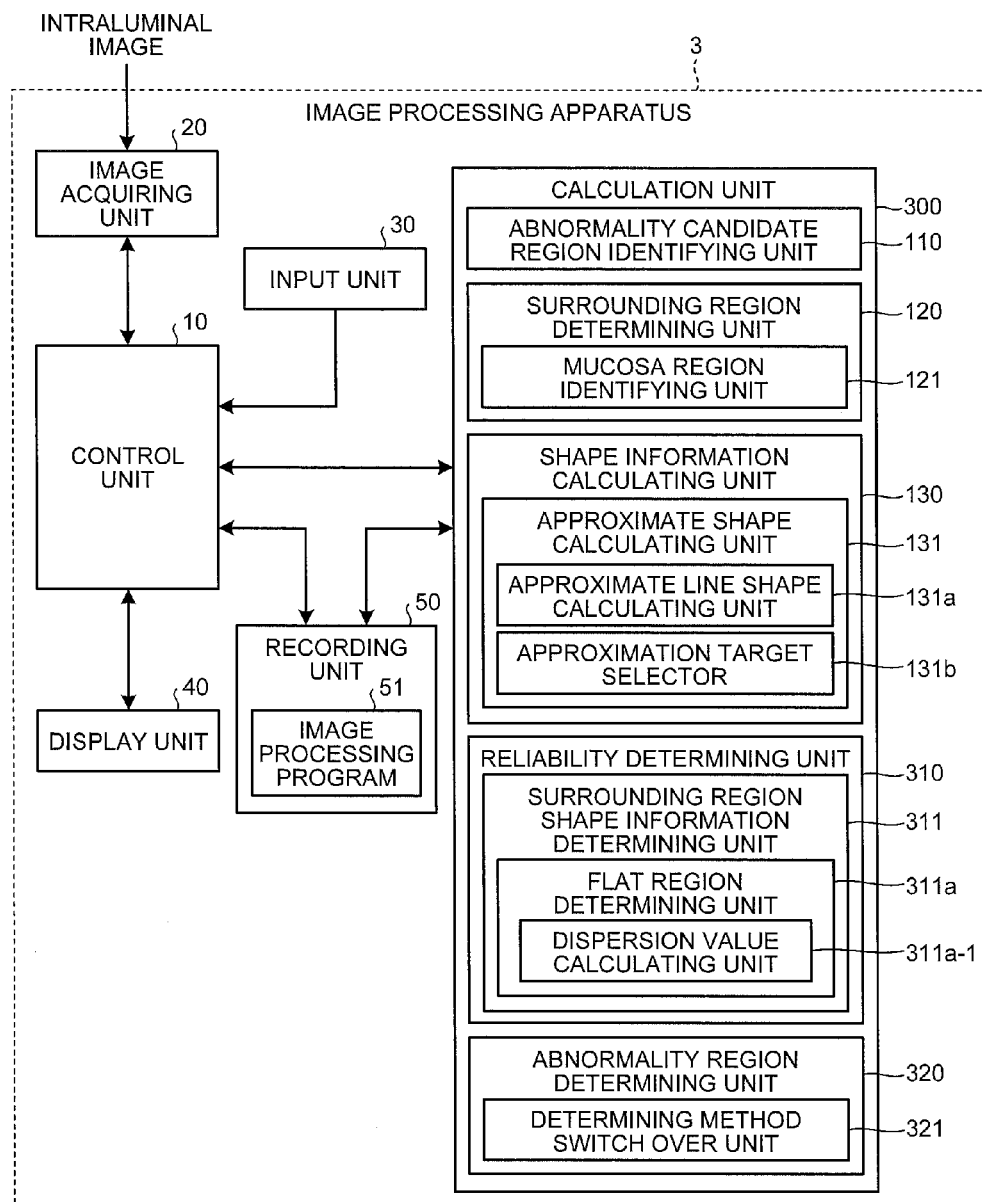
FIG. 20 is a block diagram illustrating a configuration of an image processing apparatus according to a third embodiment of the present invention.

FIG. 20 is a block diagram illustrating a configuration of an image processing apparatus according to the third embodiment of the present invention. As illustrated in FIG. 20, an image processing apparatus 3 according to the third embodiment includes a calculation unit 300, instead of the calculation unit 100 illustrated in FIG. 1.

In contrast to the calculation unit 100 illustrated in FIG. 1, the calculation unit 300 further includes, a reliability determining unit 310 that determines reliability of abnormality region determination based on shape information, and further includes an abnormality region determining unit 320, instead of the abnormality region determining unit 140 illustrated in FIG. 1. A configuration of each unit of the calculation unit 300 and image processing apparatus 3, other than the reliability determining unit 310 and the abnormality region determining unit 320, is similar to that of the first embodiment.

The reliability determining unit 310 has a surrounding region shape information determining unit 311 that determines the reliability based on shape information of a surrounding region. The surrounding region shape information determining unit 311 has a flat region determining unit 311a that includes a dispersion value calculating unit 311a-1 and determines the reliability, based on whether or not the surrounding region is a flat region.

The abnormality region determining unit 320 has a determining method switch over unit 321 that switches over, based on a result of the determination of the reliability, a determining method for determining whether or not the candidate region is an abnormality, and performs determination with respect to an abnormality by the determining method according to the result of the determination of the reliability.

Next, operations of the image processing apparatus 3 will be described.

Figure 21:
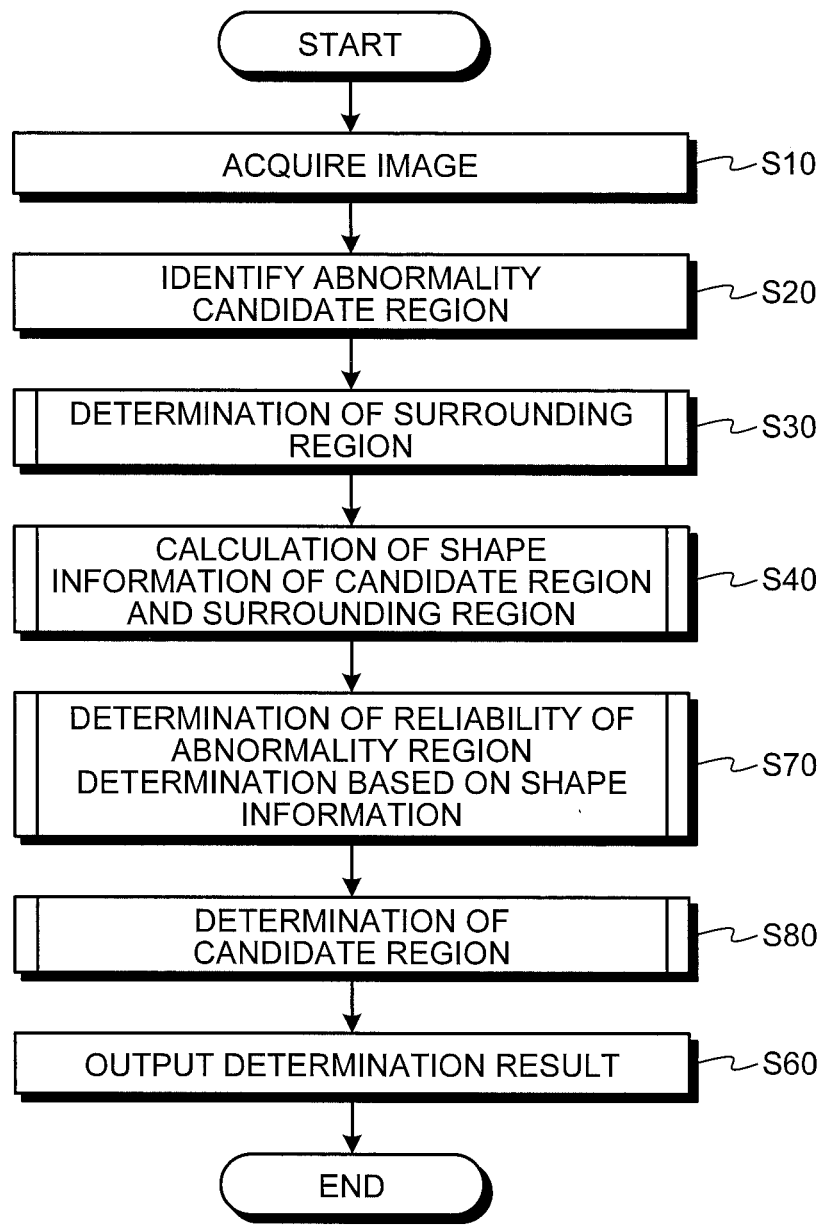
FIG. 21 is a flow chart illustrating operations of the image processing apparatus illustrated in FIG. 20.

FIG. 21 is a flow chart illustrating the operations of the image processing apparatus 3. Steps S10 to S40 and S60 illustrated in FIG. 21 correspond to those illustrated in FIG. 2.

At Step S70 subsequent to Step S40, the reliability determining unit 310 determines reliability of abnormality region determination based on shape information. If a surrounding region, which is a mucosal surface, is a flat region, even if a residue is floating above it, a difference in shapes between the residue and mucosal surface is difficult to be caused. In that case, if an attempt is made to determine, based simply on shape information of a candidate region and a surrounding region, whether or not the candidate region is an abnormality, accuracy of the determination may be reduced. Thus, in this third embodiment, determination of a reliability is performed based on shape information of a surrounding region, and according to a result thereof, determination with respect to a candidate region is performed.

Figure 22:
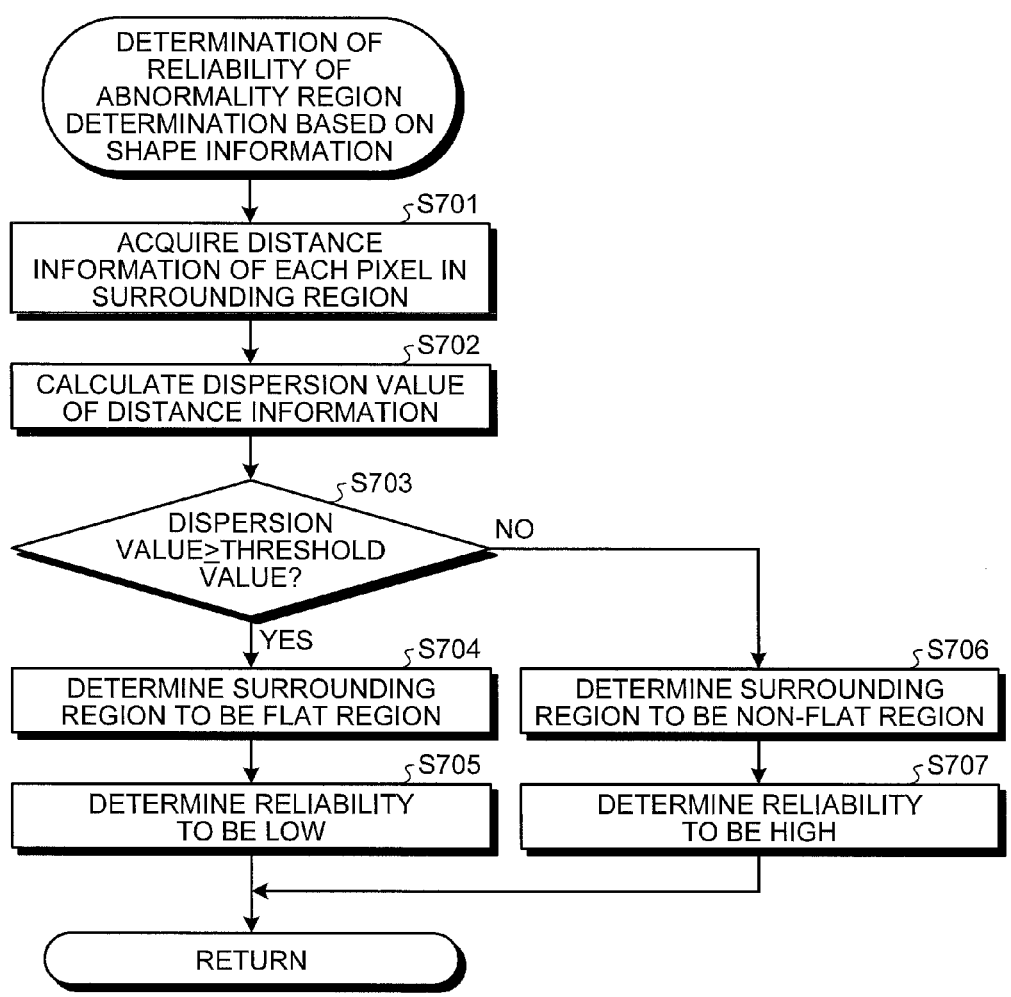
FIG. 22 is a flow chart illustrating a process of determining reliability of abnormality region determination based on shape information.

FIG. 22 is a flow chart illustrating details of a process of determining reliability of abnormality region determination based on shape information.

First, at Step S701, the surrounding region shape information determining unit 311 acquires distance information of the surrounding region in the depth direction determined in Step S30. As the distance information, an R-value, which is a wavelength component that is hard to be absorbed and scattered in a body, luminance calculated from pixel values (respective values of R, G, and B components), or the like, is used.

At subsequent Step S702, the dispersion value calculating unit 311a-1 calculates a dispersion value of the distance information of the surrounding region.

At Step S703, the flat region determining unit 311a determines whether or not the calculated dispersion value of the distance information is equal to or greater than a specified threshold value. If the dispersion value is equal to or greater than the threshold value (Step S703: Yes), it is determined that the surrounding region is a flat region (Step S704). According to this, the reliability determining unit 310 determines, if determination of an abnormality region based on the shape information is performed with respect to a candidate region near that surrounding region, that reliability of the determination is low (Step S705).

On the contrary, if the calculated dispersion value of the distance information is less than the threshold value (Step S703: No), the flat region determining unit 311a determines that the surrounding region is not a flat region (is a non-flat region) (Step S706). According to this, the reliability determining unit 310 determines, if determination of an abnormality region based on the shape information is performed with respect to a candidate region near that surrounding region, that reliability of the determination is high (Step S707). Thereafter, the process returns to the main routine.

At Step S80, any method other than the method of using the dispersion value may be used, as long as determination of whether or not the surrounding region is a flat region is possible. For example, an absolute value of a slope of a line segment calculated as the shape information of a surrounding region may be compared with a specified threshold value, and if the absolute value of the slope is less than a threshold value, the surrounding region may be determined to be a flat region.

Figure 23:
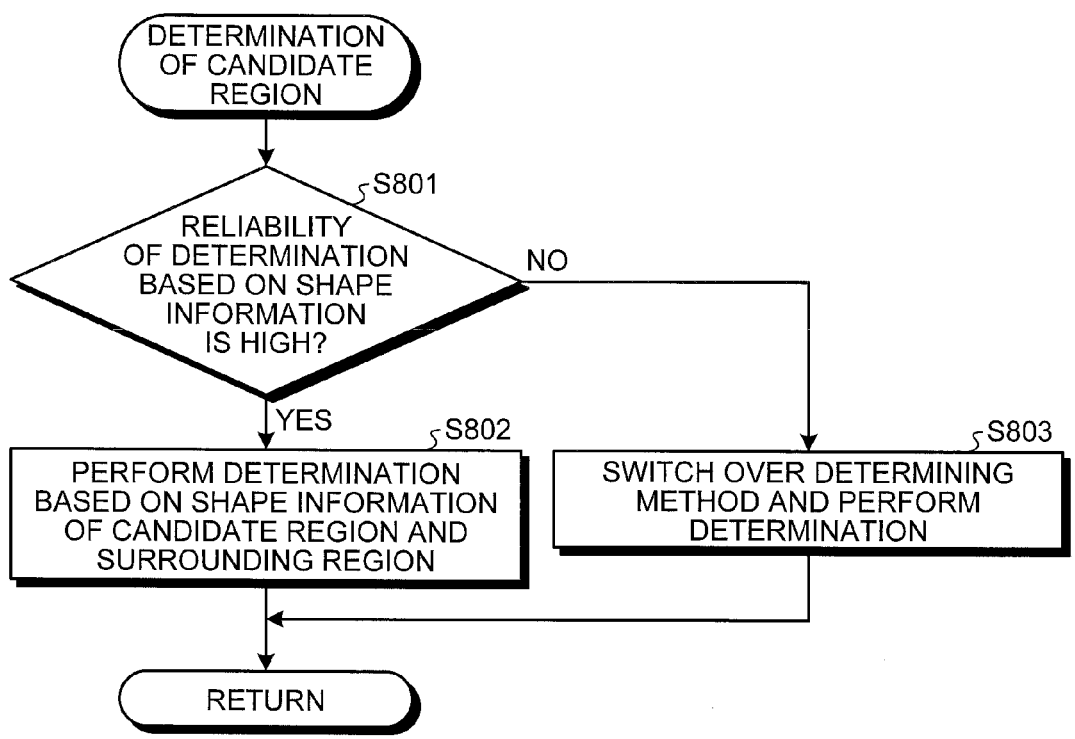
FIG. 23 is a flow chart illustrating a process of determining a candidate region.

At Step S80 subsequent to Step S70, the abnormality region determining unit 320 performs, based on a result of the determination in Step S70, determination of whether or not the candidate region is an abnormality. FIG. 23 is a flow chart illustrating details of that process.

If the reliability of the determination based on the shape information is high (Step S801: yes), the abnormality region determining unit 320 performs, based on the shape information of the candidate region and surrounding region (that is, the slopes of the line segments in the respective directions passing the gravity center), determination of whether or not the candidate region is an abnormality (Step S802). Details of this determining process are the same as those of the process in Step S50 of FIG. 2.

On the contrary, if the reliability of the determination based on the shape information is low (Step S801: No), the abnormality region determining unit 320 switches over the method of determining the candidate region to a method other than the method based on the shape information (Step S803). Thereafter, the process returns to the main routine.

For Step S803, various methods, such as a determination method based on texture feature data inside a candidate region, may be used. As an example, a method of determining a candidate region, based on texture feature data, will be described below.

First, the abnormality region determining unit 320 calculates, as texture feature data inside a candidate region, for example, size of a particular frequency component calculated by discrete cosine transform (DCT), discrete Fourier transform (DFT), Gabor filtering, or the like.

Subsequently, the abnormality region determining unit 320 determines whether or not the texture feature data in the candidate region indicate homogeneity. Homogeneity of texture feature data can be evaluated by a distance (hereinafter, referred to as "coordinate gravity center distance") between a coordinate gravity center of a candidate region and a coordinate gravity center obtained by weighting each pixel in the candidate region by the texture feature data. In more detail, a coordinate gravity center ($G_x$, $G_y$) obtained by weighting each pixel in a candidate region by texture feature data is given by Equation (5) below, by using a coordinate gravity center ($g_x$, $g_y$) of a candidate region, coordinates ($x_i$, $y_i$) of an i-th pixel in the candidate region, and texture feature data $T_i$ of the i-th pixel.

$$\begin{cases} G_x = \dfrac{\sum_{i=1}^{N} X_i T_i}{\sum_{i=1}^{N} T_i} \\ G_y = \dfrac{\sum_{i=1}^{N} X_i T_i}{\sum_{i=1}^{N} T_i} \end{cases} \quad (5)$$

In Equation (5), "N" is the number of pixels in the candidate region and i=1 to "N".

Accordingly, the coordinate gravity center distance "D" is given by Equation (6) below.

$$D = \sqrt{(G_x - g_x)^2 + (G_y - g_y)^2} \quad (6)$$

If the texture feature data are homogeneous, the weighted coordinate gravity center ($G_x$, $G_y$) approximately coincides with the coordinate gravity center ($g_x$, $g_y$), and thus the value of the coordinate gravity center distance "D" becomes small. On the contrary, if the texture feature data is not homogeneous, the weighted coordinate gravity center ($G_x$, $G_y$) is separate from the coordinate gravity center ($g_x$, $g_y$), and thus the value of the coordinate gravity center distance "D" becomes large. Therefore, the abnormality region determining unit 320 compares the coordinate gravity center distance "D" with a specified threshold value, and if the coordinate gravity center distance "D" is equal to or less than the threshold value, the abnormality region determining unit 320 determines that the texture feature data are homogenous and that the candidate region is an abnormality on a mucosal surface. On the contrary, if the coordinate gravity center distance "D" is greater than the threshold value, the abnormality region determining unit 320 determines that the texture feature data are not homogenous, and that the candidate region is a floating residue.

The image processing apparatuses according to the first to third embodiments and the first to sixth modified examples thereof may be realized by executing an image processing program recorded in a recording device by a computer system, such as a personal computer or work station. Further, such a computer system may be used by being connected to another computer system or a device, such as a server, via a local area network/wide area network (LAN/WAN), or a public network, such as the Internet. In this case, the image processing apparatuses according to the first to third embodiments may acquire image data of intraluminal images via these networks, output image processing results to various output devices (viewers, printers, and the like) connected via these networks, or store the image processing results in storages devices (recording devices and reading devices thereof, or the like) connected via these networks.

The present invention is not limited to the first to third embodiments and the first to sixth modified examples thereof, and various inventions may be formed by combining a plurality of structural elements disclosed in the respective embodiments and modified examples. For example, formation by excluding some of the structural elements from the whole structural elements illustrated in the respective embodiments and modified examples may be made, or formation by combining as appropriate the structural elements illustrated in the different embodiments and modified examples may be made.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus, comprising:
an abnormality candidate region identifying unit configured to identify a candidate region for an abnormality based on color feature data from an image obtained by imaging inside of a lumen of a living body;
a surrounding region determining unit configured to determine a surrounding region surrounding the candidate region:
a shape information calculating unit configured to calculate shape information of the candidate region and shape information of the surrounding region, according to a pixel position and a distance in a depth direction with respect to a screen:
an abnormality region determining unit configured to perform a determination of whether the candidate region is an abnormality or a residue, based on a correlation between the shape information of the candidate region and the shape information of the surrounding region; and
a control unit configured to control a display to display a result of the determination of whether the candidate region is the abnormality or the residue.

2. The image processing apparatus according to claim 1, wherein
the surrounding region determining unit includes a mucosa region identifying unit configured to identify a mucosa region included in the image, and
the surrounding region determining unit determines the surrounding region from within the mucosa region.

3. The image processing apparatus according to claim 1, wherein
the surrounding region determining unit includes a gradient strength calculating unit configured to calculate a gradient strength based on pixel values of a plurality of pixels in the image, and
the surrounding region determining unit determines the surrounding region from a region in which the gradient strength is equal to or less than a specified value.

4. The image processing apparatus according to claim 1, wherein
the surrounding region determining unit includes:
a feature data calculating unit configured to calculate, based on a pixel value of each pixel in the image, feature data of each pixel; and
a region dividing unit configured to divide the image into different regions such that pixels whose difference in feature data is within a specified range belong to a same region, and
the surrounding region determining unit determines the surrounding region for each of the different regions.

5. The image processing apparatus according to claim 4, wherein the feature data calculating unit includes a distance information calculating unit configured to calculate distance information based on the pixel value of each pixel.

6. The image processing apparatus according to claim 4, wherein the feature data calculating unit includes a color feature data calculating unit configured to calculate color feature data based on the pixel value of each pixel.

7. The image processing apparatus according to claim 4, wherein the feature data calculating unit includes a texture feature data calculating unit configured to calculate texture feature data based on the pixel value of each pixel.

8. The image processing apparatus according to claim 1, wherein the shape information calculating unit includes an approximate shape calculating unit configured to approximate each of shapes of the candidate region and the surrounding region in the depth direction, to an one-dimensional or two-dimensional shape, based on pixel values of a plurality of pixels included in each of the candidate region and the surrounding region.

9. The image processing apparatus according to claim 8, wherein the approximate shape calculating unit includes an approximate line shape calculating unit configured to approximate each of the shapes of the candidate region and the surrounding region in the depth direction, to at least one straight line or curve, based on the pixel values of the plurality of pixels.

10. The image processing apparatus according to claim 8, wherein the approximate shape calculating unit includes an approximate surface shape calculating unit configured to approximate each of the shapes of the candidate region and the surrounding region in the depth direction, to a two-dimensional shape, based on the pixel values of the plurality of pixels.

11. The image processing apparatus according to claim 8, wherein the approximate shape calculating unit further includes an approximation target selector configured to select a target for which an approximate shape is to be calculated, based on information on pixels included in the candidate region and the surrounding region.

12. The image processing apparatus according to claim 1, further comprising a reliability determining unit configured to determine reliability of abnormality region determination based on the shape information of the surrounding region, wherein
the abnormality region determining unit includes a determining method switch over unit configured to switch over a determining method of determining whether or not the candidate region is an abnormality based on a result of the determination of the reliability.

13. The image processing apparatus according to claim 12, wherein the reliability determining unit includes a surrounding region shape information determining unit configured to determine the reliability based on the shape information of the surrounding region.

14. The image processing apparatus according to claim 13, wherein the surrounding region shape information determining unit: includes a flat region determining unit configured to determine whether or not the surrounding region is a flat region; and determines that the reliability is low if the surrounding region is a flat region.

15. The image processing apparatus according to claim 14, wherein the flat region determining unit: includes a dispersion value calculating unit configured to calculate a dispersion value of pixel values of a plurality of pixels in the surrounding region; and performs the determination based on the dispersion value.

16. An image processing method, comprising:
    identifying a candidate region for an abnormality based on color feature data from an image obtained by imaging inside of a lumen of a living body:
    determining a surrounding region surrounding the candidate region:
    calculating shape information of the candidate region and shape information of the surrounding region, according to a pixel position and a distance in a depth direction with respect to a screen:
    perform a determination of whether the candidate region is an abnormality or a residue, based on a correlation between the shape information of the candidate region and the shape information of the surrounding region; and
    control a display to display a result of the determination of whether the candidate region is the abnormality or the residue.

17. A non-transitory computer-readable recording device with an executable program stored thereon, the program instructing a processor to perform:
    identifying a candidate region for an abnormality based on color feature data from an image obtained by imaging inside of a lumen of a living body:
    determining a surrounding region surrounding the candidate region:
    calculating shape information of the candidate region and shape information of the surrounding region, according to a pixel position and a distance in a depth direction with respect to a screen;
    performing a determination of whether the candidate region is an abnormality or a residue, based on a correlation between the shape information of the candidate region and the shape information of the surrounding region; and
    controlling a display to display a result of the determination of whether the candidate region is the abnormality or the residue.

18. The image processing apparatus according to claim 1, wherein the abnormality region detecting unit is configured to:
    determine that the candidate region is an abnormality when the shape information of the candidate region and the shape information of the surrounding region are similar to each other; and
    determine that the candidate is a residue when the shape information of the candidate region and the shape information of the surrounding region are not similar to each other.

19. The image processing apparatus according to claim 18,
    wherein the surrounding region is a surround mucosal surface,
    wherein the shape information of the candidate region is a gradient of the candidate region and the shape information of the surrounding region is a gradient of the surrounding region, determined according to the pixel position and the distance in the depth direction with respect to the screen, and
    wherein the abnormality region detecting unit is configured to determine whether the candidate region is an abnormality or residue based on the gradient of the candidate region and the gradient of the surrounding region.

* * * * *